United States Patent [19]
Saito et al.

[11] Patent Number: 6,124,139
[45] Date of Patent: Sep. 26, 2000

[54] METHOD AND APPARATUS FOR INDIRECT AGGLUTINATION IMMUNOASSAY

[75] Inventors: Tomoo Saito; Yoshihiro Kinoshita, both of Tokyo, Japan

[73] Assignee: Fujirebio Inc., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/933,583

[22] Filed: Sep. 19, 1997

Related U.S. Application Data

[63] Continuation of application No. 08/242,717, May 13, 1994, abandoned.

[30] Foreign Application Priority Data

May 17, 1993 [JP] Japan .................................. 5-139076
May 17, 1993 [JP] Japan .................................. 5-139082

[51] Int. Cl.[7] .................................................. G01N 33/533
[52] U.S. Cl. ........................... 436/539; 356/39; 356/383; 422/73; 422/102; 436/518; 436/526; 436/805; 436/806; 436/809
[58] Field of Search ....................... 356/39, 383; 422/73, 422/102; 436/518, 526, 805, 806, 809, 539

[56] References Cited

U.S. PATENT DOCUMENTS 4,148,607  4/1979  Bernoco et al. .......................... 424/1 X
4,373,931  2/1983  Takekawa .............................. 436/539

FOREIGN PATENT DOCUMENTS

| | | |
|---|---|---|
| 0198327A2 | of 0000 | European Pat. Off. . |
| 0198327A3 | of 0000 | European Pat. Off. . |
| 0301583A2 | of 0000 | European Pat. Off. . |
| 0301583A3 | of 0000 | European Pat. Off. . |
| 0351857A2 | of 0000 | European Pat. Off. . |
| 0426170A1 | of 0000 | European Pat. Off. . |
| 0522322A1 | of 0000 | European Pat. Off. . |
| 0 396 115 | 7/1990 | European Pat. Off. . |
| 4013586A1 | of 0000 | Germany . |
| 215725A | of 0000 | United Kingdom . |
| 8502259 | of 0000 | WIPO . |
| WO9205443 | of 0000 | WIPO . |

*Primary Examiner*—Christopher L. Chin
*Assistant Examiner*—Bao-Thuy L. Nguyen
*Attorney, Agent, or Firm*—Oblon, Spivak, McClelland, Maier & Neustadt, P.C.

[57] ABSTRACT

A method of indirect agglutination immunoassay includes, allowing particles of a reagent for immunoassay to precipitate in bottoms of at least one well, inclining the well at a specified angle to form a precipitation pattern due to a flow of the particles in the bottom of the well due to a flow of the particles, relatively moving the well and a sensor in the direction of substantially vertical to a flow direction of the formed precipitation pattern, measuring the lengths of the formed precipitation pattern at a plurality of sections within the scope of the well, and judging the occurrence of an immunoreaction based on the values of the measured length of the precipitation patterns.

3 Claims, 12 Drawing Sheets

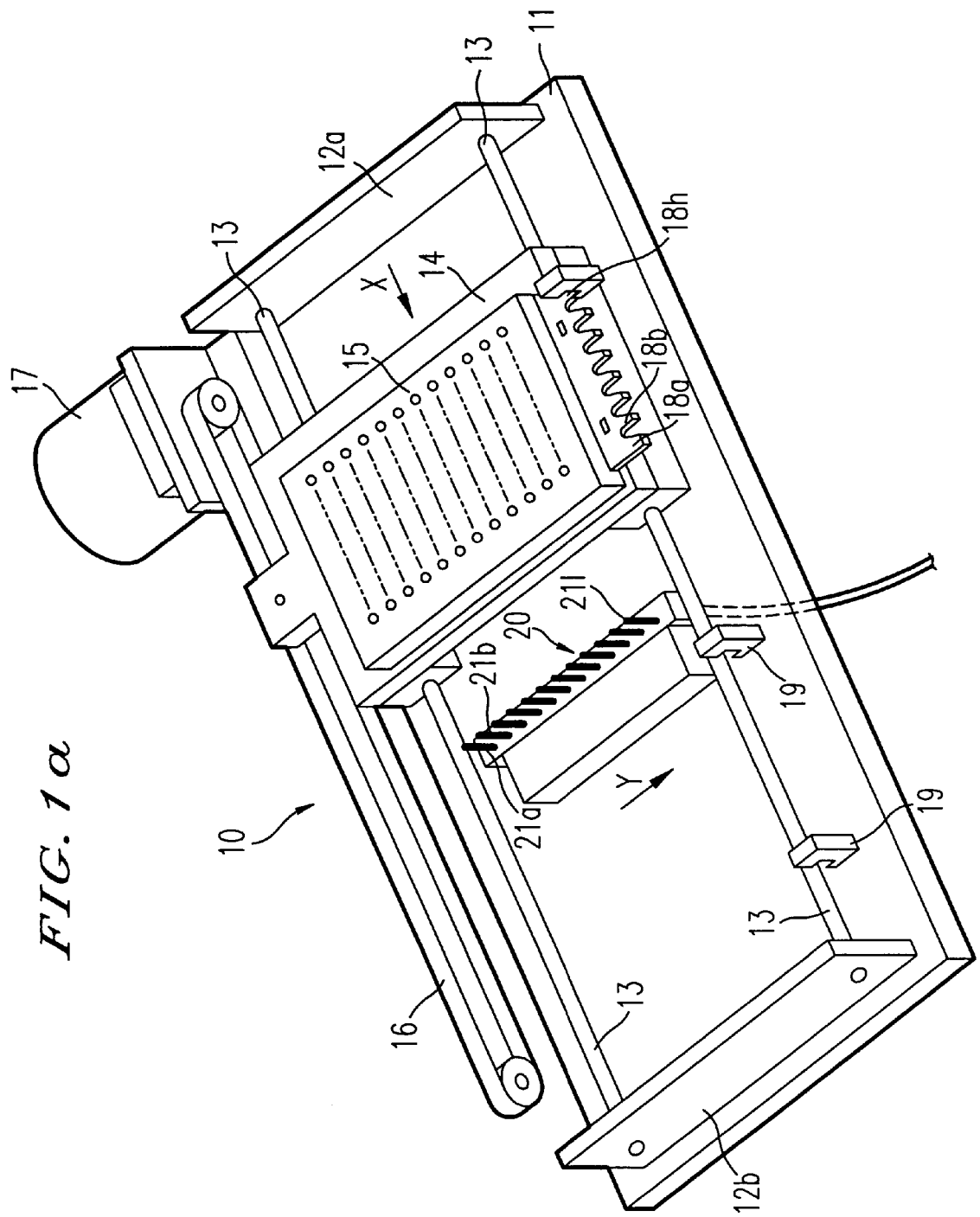
FIG. 1α

METHOD AND APPARATUS FOR INDIRECT AGGLUTINATION IMMUNOASSAY

This is a continuation division of application Ser. No. 08/242,717 filed May 13, 1994 now abandoned.

BACKGROUND OF THE INVENTION

1. Field of the Invention

The present invention relates to a method and apparatus for indirect agglutination immunoassay in which agglutination being caused by an antigen-antibody reaction is assayed using magnetic particles or magnetic-material-containing particles that have an antigen or antibody bound thereto.

2. Description of the Related Art

The inventors of the present invention previously proposed an effective method and apparatus for indirect agglutination immunoassay as U.S. patent application Ser. No. 08/082,373 "INDIRECT AGGLUTINATION IMMUNOASSAY AND APPARATUS THEREFOR" filed on Jun. 28, 1993 which is a Continuation-in-Part Application of U.S. patent application Ser. No. 07/606,205 filed on Oct. 31, 1990. According to the method, a solution of the particles of a specified reagent is added and mixed with a diluted solution of a specified sample in each of wells with a U- or V-shaped bottom in a micro plate and, after some reaction, components including the particles are precipitated in the bottom of each well by magnetic force and, subsequently, the micro plate is inclined to judge the occurrence of an immunoreaction in view of the profile of separation of the precipitated particles from the wells.

The precipitation patterns that are to be formed in the method of indirect agglutination immunoassay due to the flow of the particles in the micro plate are roughly divided into three types: i) a reaction-positive precipitation pattern that results from the bonding among particles due to an immunoreaction and which is characterized by stationary particles that do not move but which remain as a spot in the bottom of each well even if the micro plate is inclined; ii) a reaction-negative precipitation pattern that results from the non-binding among particles due to the absence of an immunoreaction and which is characterized by free-flowing particles that, upon inclination of the micro plate, flow down to the side wall of each well; and iii) a precipitation pattern intermediate between i) and ii).

The precipitation patterns due to the flow of the particles that are formed in the bottoms of wells in a micro plate can be read by various methods such as taking a picture of the micro plate from above with a TV camera or, alternatively, using a line sensor and taking a picture of the precipitation patterns due to the flow of the particles by image processing techniques for measuring the flow lengths of the respective patterns due to the flow of the particles so that they can be correlated to the occurrence or non-occurrence of an immunoreaction.

The method of indirect agglutination immunoassay filed as the U.S. patent application Ser. No. 08/082,373 is efficient in that it is capable of judging the occurrence of an immunoreaction in a shorter time and with higher precision than other approaches such as a standing method in which particles are allowed to precipitate under gravity within wells in a micro plate and in which judgement for the occurrence of an antigen-antibody reaction is made on the basis of the precipitation pattern of the particles. However, in the practice of this method, it is essential that the precipitation patterns due to the flow of the particles be read by a TV camera, a line sensor or the like.

A major problem with the methods of picking up image with a TV camera, a line sensor or the like is that the distance which have to be provided between the TV camera, line sensor or the like and the micro plate makes it imperative to use a large device for judging precipitation patterns; if the distance between the two elements is unduly short, particularly in the case where the micro plate has U- or V-shaped wells, the distance to the TV camera, line sensor or the like is not invariable in the center of the bottom of each well and its peripheral portion and, hence, defocusing occurs to cause disadvantages such as distorted image.

Glass or synthetic resin (e.g., polystyrene) micro plate used in indirect agglutination immunoassay has in most cases a plurality of wells with U- or V-shaped bottoms and the micro plate has ninety six wells (in 12 columns ×8 rows). When molding micro plates, the wells which are formed to have U- or V-shaped bottoms may unavoidably experience molding distortion at the edges on the periphery of well's bottom and, hence, the wells formed may not necessarily lie on one straight line in the direction of columns or rows. Accordingly, even if the sensor is moved along the central part of the bottom of each well in the direction of either columns or rows after the formation of precipitation patterns, the above-mentioned misalignment introduces inaccuracy in the measurement of the length of precipitation patterns.

Thus, the misalignment in the wells that are formed by molding a micro plate reduces the precision in the measurement of precipitation patterns due to the flow of the particles which provide criteria for the occurrence of an immunoreaction, is the correct judgement for the occurrence of an immunoreaction provided and the reproducibility of data is fluctuated greatly.

In addition, irrespective of the V- or U-shape micro plate is used to judge for the occurrence of an immunoreaction by indirect agglutination techniques, precipitation patterns due to the flow of particles are formed on slopes that extend from the centers of the bottoms of respective wells.

Therefore, when the lengths of precipitation patterns due to the flow of the particles formed on the slopes of the wells are to be read optically with a sensor or the like, a defocusing problem may occur since the distance to the sensor differs between the center of each well and its periphery.

SUMMARY OF THE INVENTION

It is an object of the present invention to provide a method of indirect agglutination immunoassay and apparatus therefor that is capable of precise measurement of the length of precipitation patterns due to the flow of particles even if the plurality of wells formed in a micro plate to be used in the practice of an indirect agglutination test are misaligned on account of molding errors.

It is another object of the present invention to provide a method and apparatus for indirect agglutination immunoassay which when making optical judgement, are easy to operate as exemplified by the absence of any difference in the distance to the sensors between the center of each well and its periphery and by the ability to form spindle-shaped precipitation patterns without sharp-pointed advancing ends which are advantageous for the purpose of correct measurements.

In order to achieve the first mentioned object, a method of indirect agglutination immunoassay includes the steps of: providing a micro plate holder on which a micro plate including a plurality of wells that are arranged substantially in linear in columns and rows in the micro plate is provided on a base body; providing a sensor block having the same number of aligned sensors as the wells formed in at least one of the columns or rows in the micro plate in a position downstream from the direction of movement of the micro plate holder to cross at a right angle to the direction of movement of the micro plate holder; measuring a plurality of sections of the well within the scope of the well before inclining the well; inclining one of said micro plate holder and the micro plate to form the precipitation patterns due to the flow of the particles in the bottoms of respective wells in the micro plate; relatively moving the micro plate and the sensor block in which each of the well and each of the sensor corresponding to the well moves relatively within the scope of each well at the predetermined distance to measure the lengths of the precipitation pattern due to the flow of the particles at plurality of sections with crossing at right angles the direction of flow for the formed precipitation patterns; comparing the measured values of the lengths off the precipitation pattern due to the flow of the particles to each other in each well to obtain the longest value of the measured values of the length of precipitation pattern due to the flow of the particles for each well; and judging the occurrence of an immunoreaction based on the obtained longest value of the length of the precipitation pattern due to the flow of the particles for each well; wherein the micro plate holder is movable in the direction of the inclination.

For example, the particles of a reagent for immunoassay that may be used in the present invention are magnetic particles, gelatin particles containing a ferromagnetic medium, particles having a magnetic medium coated with serum albumin, particles having a magnetic medium coated with a synthetic polymer, particles having a magnetic medium contained in a synthetic polymer, and particles described in the Examined Japanese Patent Publication No. Sho 63-29223 which are the gelatin particles, red corpuscles from various animals as rabbit, sheep, goat or the like, inorganic particles such as those of silica and kaolin and the like.

These particles may be allowed to precipitate in the bottoms of respective wells in a micro plate by either magnetic or centrifugal force. From the viewpoint of automating the procedure of immunoassay, various kinds of magnetic particles are desirably used to allow them to be precipitated by magnetic force.

The sections to be searched for the measurement of the length of precipitation patterns in the direction of the flow of the particles in the respective wells in the micro plate are such that the distance between a circumferential point in each well that is forward in the direction of flow of particles and a backward circumferential point that corresponds to said forward point is measured at a plurality of points by moving the micro plate or optical sensors in small increments in such a way that they cross the direction of particle flow at right angles.

Precipitation patterns can be formed in the bottoms of wells either by centrifugal force or inclining the micro plate using an appropriate method. In the latter case, the micro plate is inclined at an angle of 50 to 70° in the direction in which the particles flow.

In the case where the wells in the micro plate have V-shaped bottoms, precipitation patterns can be formed efficiently by insuring that the planes in which the precipitation patterns are to be formed are inclined at angles of 20 to 40° with respect to the horizontal direction.

The lengths of precipitation patterns, as well as the sections to be searched for the measurement of the lengths of precipitation patterns in the direction of the flow of the particles are measured with the micro plate or optical sensors being moved in small increments in such a way that either one of them crosses the other at right angles. Specifically, the micro plate holder is mounted on the inclinable base body which includes at predetermined angle to be movable the direction of inclination and the sensor block having a plurality of aligned optical sensors provided in a position downstream to the direction of movement of the micro plate holder is adapted so that the micro plate holder is capable of passage either above or below the sensor block. With the thus constructed apparatus for measuring precipitation patterns, the sensor block is moved in a predetermined small distance at right angles within the scope of each well with respect to the direction of movement of the micro plate holder.

In this apparatus for measuring precipitation patterns, the sensor block includes the same number of aligned optical sensors as the wells formed in columns or rows in the micro plate. The optical sensors may be of various types such as transmission and reflection optical sensors. In the case of a transmission optical sensor, a light source is provided on the side of the micro plate that is away from the optical sensors; in the case of a reflection optical sensor, the light source is replaced by a reflective plate.

Stated more specifically, the sensor block is operatively associated with a shaft member on a rotor that is provided in such a way that it is kept by the urging force of a spring in contact with the outer peripheral edge of a cam member that is coupled directly to the rotating shaft of a sensor block moving motor provided below the base body and which has a plurality of arcuate portions and the same number of straight portions formed alternately on the outer periphery, and the sensor block is so adapted that the pivoting of the cam member causes it to be moved in small increments in a direction that is vertical to the direction of movement of the micro plate.

In accordance with the method of the present invention for indirect agglutination immunoassay, the particles of a reagent for immunoassay are allowed to precipitate in the bottoms of wells in a micro plate and, thereafter, the micro plate is inclined at a specified angle to form precipitation patterns in the bottoms of wells due to the flow of the particles, and the micro plate or optical sensors are moved in small increments to cross at right angles the direction of flow of the formed precipitation patterns, thereby measuring the lengths of the precipitation patterns at a plurality of points. Since the greatest pattern length of the measured lengths can be used as the length of the precipitation pattern, the intended measurement of precipitation patterns can be effected in a simple and correct way.

Particularly, when measuring the lengths of precipitation patterns, the sections to be searched for the measurement of the lengths of precipitation patterns are preliminarily measured for each well before the formation of precipitation patterns due to the flow of the component particles so as to effectively correct any errors contained in the pitch between wells in the direction of movement of the micro plate.

Further, the micro plate is inclined to form precipitation patterns in the bottoms of wells and the micro plate or optical sensors are moved in small increments to cross at right angles the direction of flow for the formed precipitation patterns so as to measure the length of those precipitation patterns at a plurality of points and this can effectively correct any errors contained in the pitch between wells in a direction vertical to the direction of movement of the micro plate.

In order to achieve the second mentioned object, a method of indirect agglutination immunoassay of the present invention including the steps of: allowing a component containing magnetic particles or particles containing a magnetic medium of a reagent for immunoassay to precipitate in the bottoms of respective wells in a micro plate by magnetic force; forming precipitation patterns in the bottoms of respective wells due to the flow of the particles and; judging the occurrence of an immunoreaction based on the formed precipitation patterns; wherein the shape of the bottom of each of the wells is flat.

The micro plate molded from synthetic resins or glass, in which the wells are flat-bottomed is also used in the present invention. The bottoms of wells can be formed flat by one of the following two methods.

The first method, which is illustrated in FIGS. 7 and 8, is that forming a well having a circular cross section, with the bottom being horizontal with respect to the vertical inner peripheral surface of the well, namely, perpendicular to said inner peripheral surface. The second method, which is illustrated in FIGS. 9 and 10, is that forming a well having a circular cross section, with the bottom being inclined in one direction with respect to the vertical inner peripheral surface of the well. The slope of inclination is preferably such as to form an angle of about 30° with the imaginary horizontal line across the opening of the well.

In the case where the well is formed with its bottom inclined in one direction with respect to the vertical inner peripheral surface of the well, the component particles are attracted by a magnet so that they are allowed to precipitate in the higher position of the inclined bottom. Thereafter, the magnetic force is canceled, whereupon the particles will flow down the slope under gravity to form a precipitation pattern. Thus, there is no need to incline the micro plate at a specified angle for the particular purpose of forming a precipitation pattern.

The magnets which are used in the present invention to allow the particles within wells to be precipitated at specified sites in the flat bottoms are provided below the respective wells. An adapter with a sharp-pointed tip is provided on top of each magnet; if desired, such adapter may be mounted detachably on each magnet, whereby one can freely adjust the position of adapter setup relative to the bottom of each well.

The adapter may be formed of a magnet per se or, alternatively, it may be formed of a magnetizable material such as iron. The magnet is provided below the associated well in such a way that the tip of the adapter will be located at a specified site under the bottom of the well.

In this case, magnets are retained by being fitted in holes that are formed in a polyvinyl chloride retainer plate in positions that are in registry with the aligned wells in the micro plate and the magnets are then fixed by attraction to the top surface of a base member in the form of an iron plate; at the same time, the retainer plate is covered with a polyvinyl chloride cover member that covers the surfaces of said magnets, except in areas where the tips of the adapters project through said cover member. In this way, the magnetic force from the surfaces of the magnets will not act on the bottoms of wells but, instead, only the magnetic force from the tips of adapters can be concentrated to act on the bottoms of wells at specified sites.

The method of the present invention for indirect agglutination immunoassay is performed using a micro plate having flat-bottomed wells formed therein and into which a diluted sample solution and the particles of a reagent are to be injected. In this method, the component particles can be allowed to precipitate at specified sites in the bottoms of the wells by magnetic force and, therefore, even if optical sensors are used to measure the lengths of precipitation patterns due to the flow of the particles, the distance from each sensor to the associated precipitation pattern can be held constant in every part of the well and, at the same time, there can be formed precipitation patterns that are spindle-shaped but which have no sharp advancing end.

The apparatus of the present invention for indirect agglutination immunoassay is characterized in that magnets fitted with adapters each having a sharp-pointed tip are provided at specified sites under the respective wells. This arrangement insures that even if the bottoms of the wells are flat, the component particles can be allowed to precipitate in specified positions.

If the bottoms of wells are inclined in one direction with respect to their vertical inner peripheral surfaces, precipitation patterns can be formed without inclining the micro plate at a specified angle.

BRIEF DESCRIPTION OF THE DRAWINGS

In the drawing;

FIG. 1(a) is a perspective view showing an example of the apparatus of the present invention for measuring precipitation patterns;

PREFERRED EMBODIMENTS OF THE INVENTION

Figure 1B:
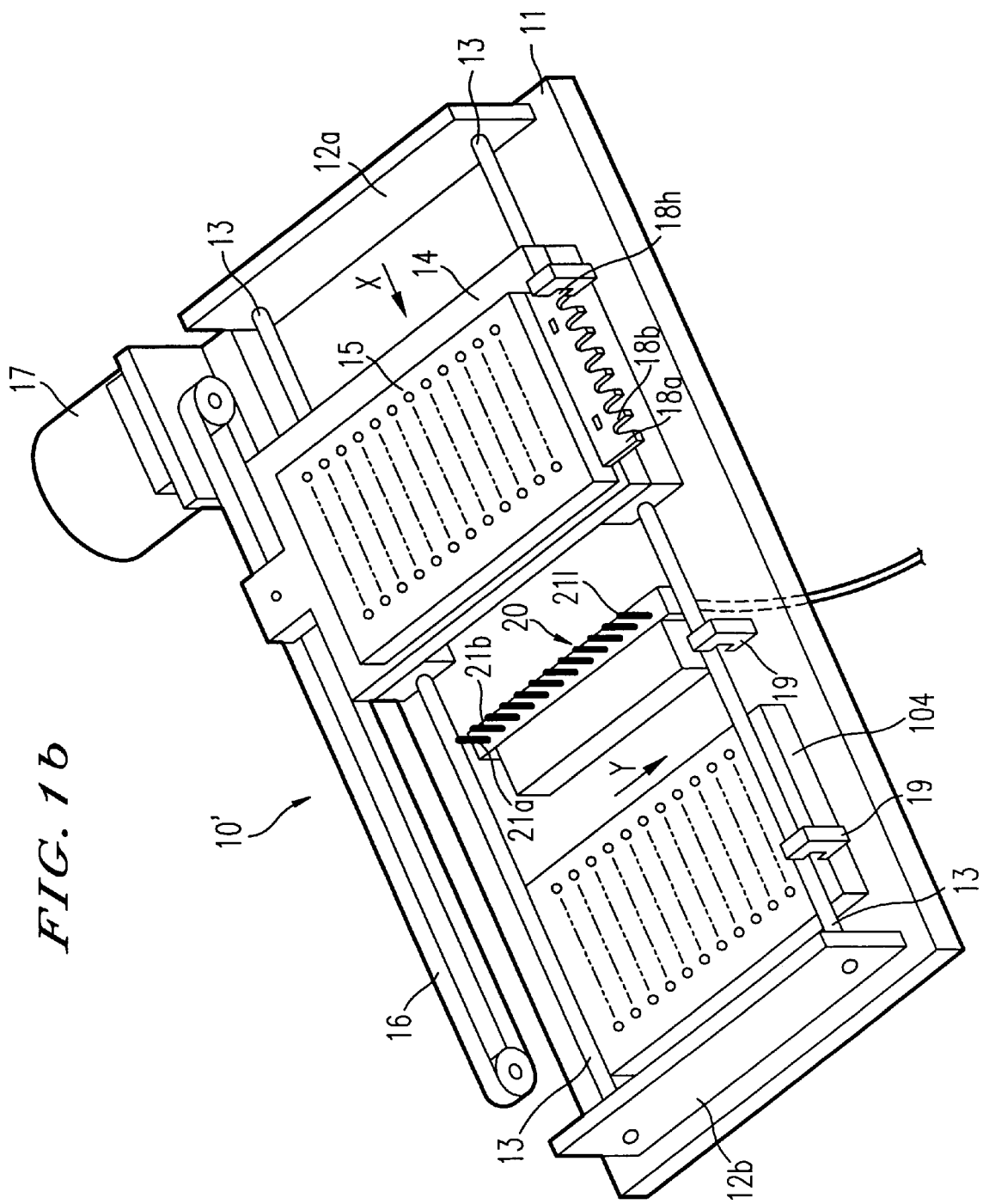
FIG. 1(b) is a perspective view showing an example of the apparatus for measuring precipitation patterns which has a magnet unit.

The preferred embodiments of the present invention of method and apparatus for indirect agglutination immunoassay will be described specifically as follows with citing the accompanying drawings.

As shown in FIG. 1, an apparatus for indirect agglutination immunoassay 10 includes a base body 11 that can incline through 60° in a specified direction, a micro plate holder 14 that moves back and forth on the base body 11 in the direction of inclination, a drive mechanism for moving the micro plate holder 14 on the base body 11, a sensor block 20 having 12 reflection optical sensors 21a, 21b, . . . , 21l mounted in one line (the number of the optical sensors is the same as that of wells in columns in a micro plate 15 that is held detachably on the micro plate holder 14), and a moving mechanism that moves the sensor block 20 over small ranges which are the scope of each well in a predetermined small distance in a direction vertical to the direction of movement of the micro plate holder 14. In this case, the number of optical sensors may be as same as that of wells in rows.

Figure 1C:
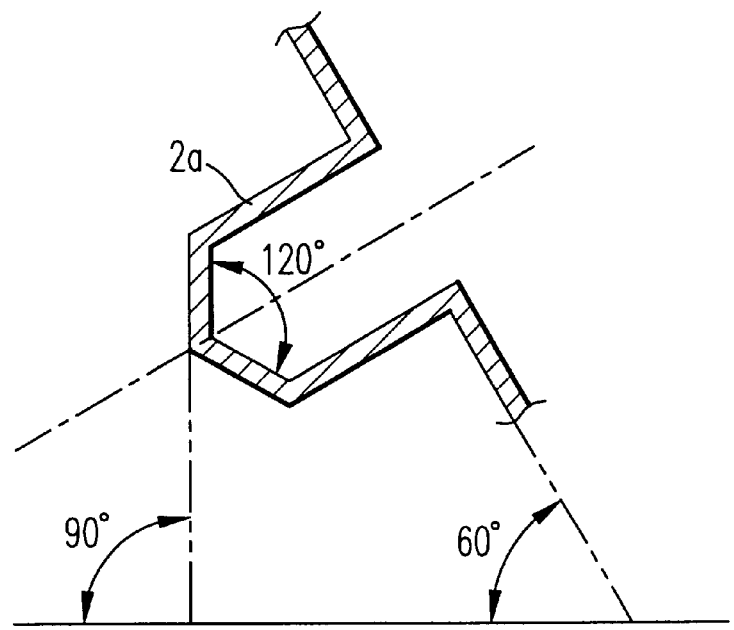
FIG. 1(c) is an explanation view showing a V-shaped bottom of a well.
Figure 1D:
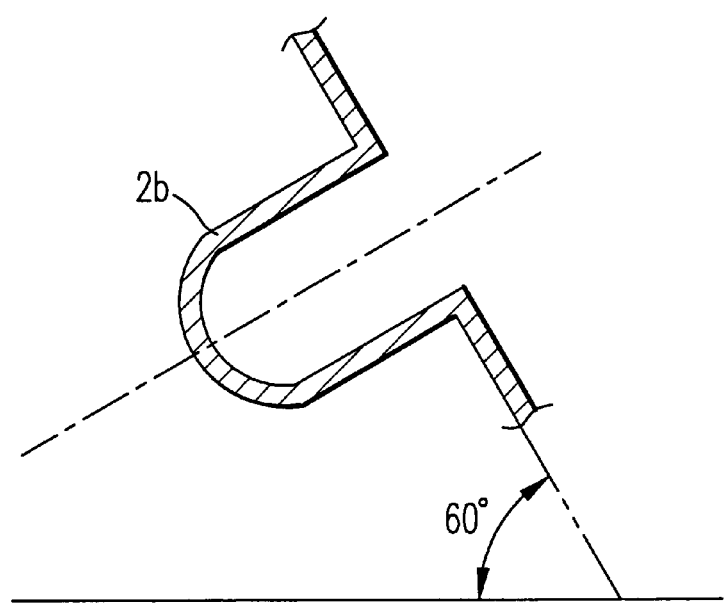
FIG. 1(d) is an explanation view showing a U-shaped bottom of the well.

In addition, as shown in FIG. 1(c) and 1(d), the well used in the embodiment have a V- or U-shaped bottom. For example, the bottom of the well 2a having the V-shaped bottom as shown in FIG. 1(c) has an angle of 120°. The well 2a is inclined at 60° so as to flow a precipitation pattern efficiently.

The base body 11 is generally shaped in a rectangular form and has guide mounting plates 12a and 12b provided along the edges of two shorter opposing sides. The guide plates 12a and 12b are connected by a pair of guide rods 13 that are spaced apart at a specified distance. The side of the guide mounting plate 12a of the base body 11 is raised to incline by an inclining mechanism (not shown) provided on the back side thereof through an angle of 70° (60° in general) with the neighborhood of the inner side of the guide mounting plate 12b serving as the basal end. In addition, the inclining mechanism can be provided on the back side of the micro plate holder 14 so that merely the micro plate holder 14 is inclined.

The micro plate holder 14 carries the detachable micro plate 15 thereon that has wells with U- or V-shaped bottoms in the central parts of which a component containing magnetic particles or particles containing a magnetic medium of a reagent for immunoassay is precipitated by magnetic force. In the process of measurement, the micro plate holder 14 slides back and forth on the base body 11 with carrying the micro plate 15 as it is guided by the pair of guide rods 13.

The micro plate 15 is a commercial product made of a synthetic resin or glass and it has a total of ninety six wells formed as integral parts in an array consisting of twelve rows along the longer side of the plate (in its longitudinal direction) and eight columns along the shorter side (in the transverse direction).

For example, as shown in FIG. 1(b), a magnet unit 104 is provided on the base body 11 at the other side, which has a plurality of magnets positions of which correspond to that of the wells of the micro plate 15. Before the inclination of the base body 11, the micro plate 15 having the wells in which the regent for immunoassay is contained is moved to position above the magnet unit 104 to correspond the wells with the magnets each other so that a component containing magnetic particles or particles containing a magnetic medium of the regent for immunoassay in each well is precipitated by the magnet force of each magnet. The micro plate 15 in which the component of the reagent is thus precipitated is returned to its former position to be inclined, thereby efficiently measuring the indirect agglutination immunoassay. Also in this case, the inclining mechanism may not be provided on the back side of the base body 11, but provided on that of the micro plate holder 14 so that merely the micro plate holder 14 is inclined.

The micro plate holder 14 is moved by a timing belt 16 provided along one lateral edge of the base body 11 in its longitudinal direction. The timing belt 16 is in operative association with a stepping motor 17 which is driven when measurement position detecting sensors 18a, 18b, . . . , 18h projecting from one lateral side of the micro plate holder 14 in the direction of its movement in positions that correspond to the number of wells along the shorter side of the micro plate 15 (eight wells are provided in the case of the example under discussion) make successive contact with measurement position sensors 19 provided downstream the direction of movement, whereupon the micro plate holder 14 advances transversely by small increments corresponding to the pitch between two adjacent columns of wells.

The sensor block 20 which measures, for each well, the sections to be searched for the measurement of the length of precipitation patterns and the lengths of precipitation patterns due to the flow of particles includes twelve reflection optical sensors 21a, 21b, . . . , 21l that are provided side by side in a row on top of the block for measuring the return light from a reflector plate (not shown) in correspondence to the twelve wells provided in the longitudinal direction of the micro plate 15. As shown in FIG. 1, the sensor block 20 is provided on the base body 11 ahead of the micro plate holder 14 so that the plate holder 14 is capable of passage above the sensor block 20 and that the sensor block 20 is capable of moving by small distances in a direction vertical to the direction of movement of the micro plate holder 14.

Figure 2:
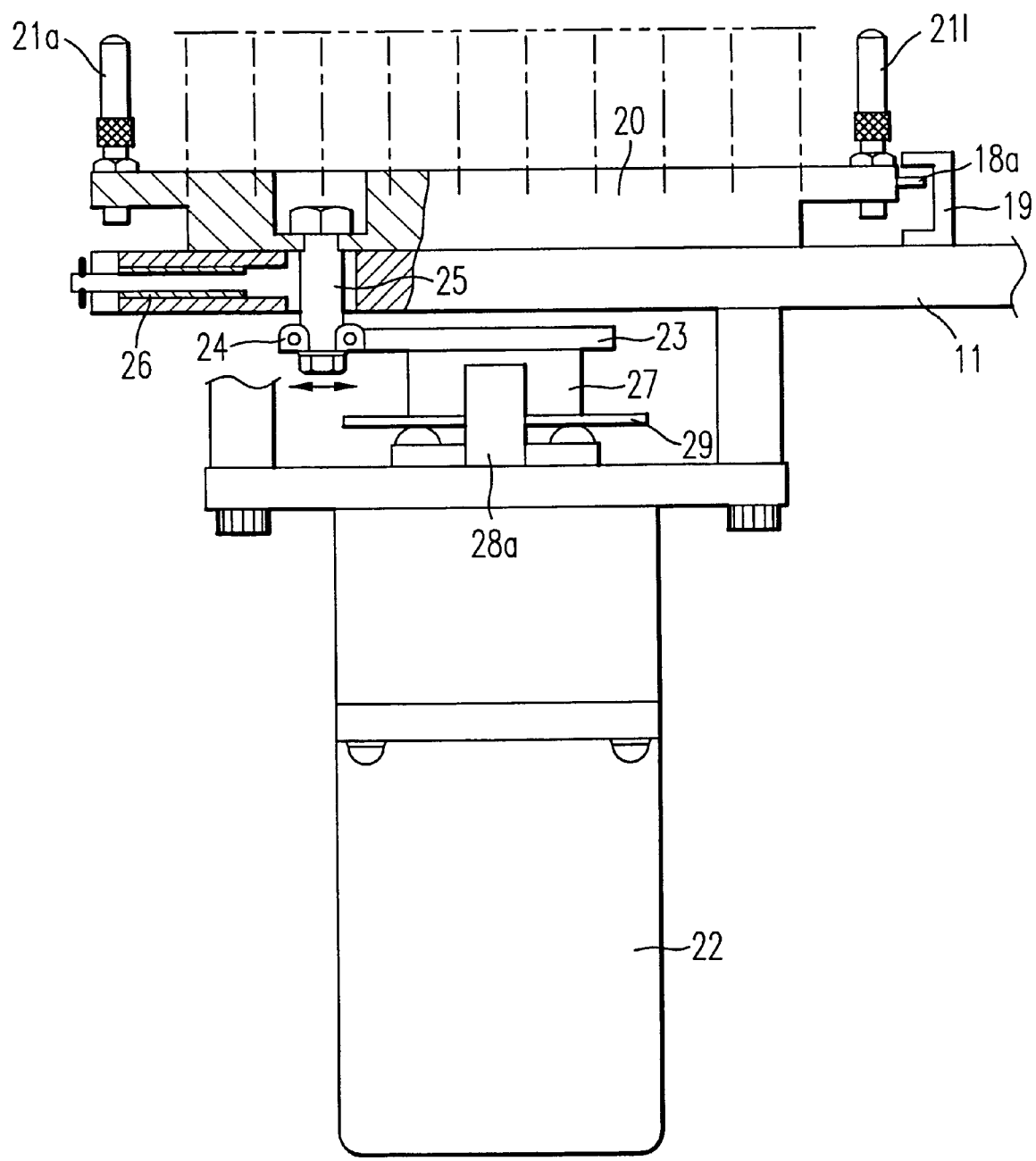
FIG. 2 is a side view showing the essential part of the apparatus for measuring precipitation patterns that is shown in FIG. 1.
Figure 3A:
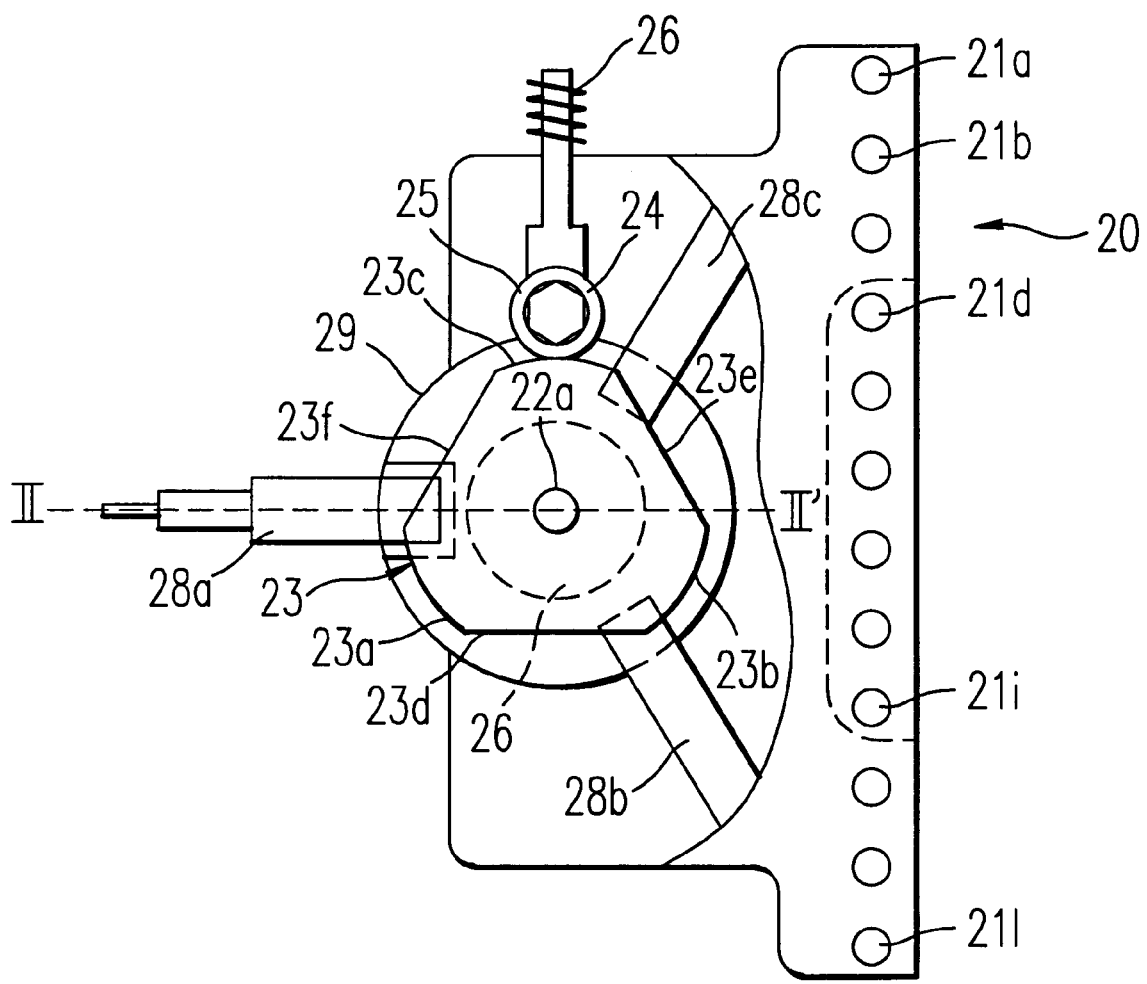
FIG. 3(a) is a plan view showing the essential part of the apparatus for measuring precipitation patterns that is shown in FIG. 1.

Stated more specifically, as shown in FIGS. 2 and 3, a motor 22 is provided below the base body 11 for moving the sensor block and the rotating shaft 22a of the motor is coupled directly to a cam member 23 that has three arcuate portions 23a, 23b and 23c formed alternately with three straight portions 23d, 23e and 23f on the outer peripheral edge. A rotor 24 that is always in contact with the outer periphery of the cam member 23 is provided on the outer peripheral edge of the same cam member 23. The basal end portion of a shaft member 25 engaging a bearing within the rotor 24 projects above the base body 11 to be in engagement with the bottom surface of the sensor block 20 and, at the same time, the shaft member 25 is urged with a spring 26 so that the rotor 24 is held always in contact with the outer periphery of the cam member 23. If the cam member 23 pivots in response to the rotation of the motor 22 and the arcuate portions 23a to 23c on the outer peripheral edge of he cam member 23 contact the rotor 24, the sensor block 20 is allowed to move by predetermined small distances of about 0.1 mm in a direction vertical to the direction of movement of the micro plate holder 14.

A cylindrical portion 27 projects from the back side of the cam member 23 and three optical sensors 28a, 28b and 28c are provided on the outer circumference of that cylindrical portion in positions that are offset from each other by 120°. A disk-shaped detector plate 29 is provided around the cylindrical portion 27 and has a cutout portion 30 formed in its outer peripheral edge. When the detector plate 29 rotates to such a position that the cutout portion 30 is in registry with either one of optical sensors 28a, 28b and 28c, the relevant optical sensor is activated to control the start or stop of the movement of the sensor block 20.

Figure 3B:
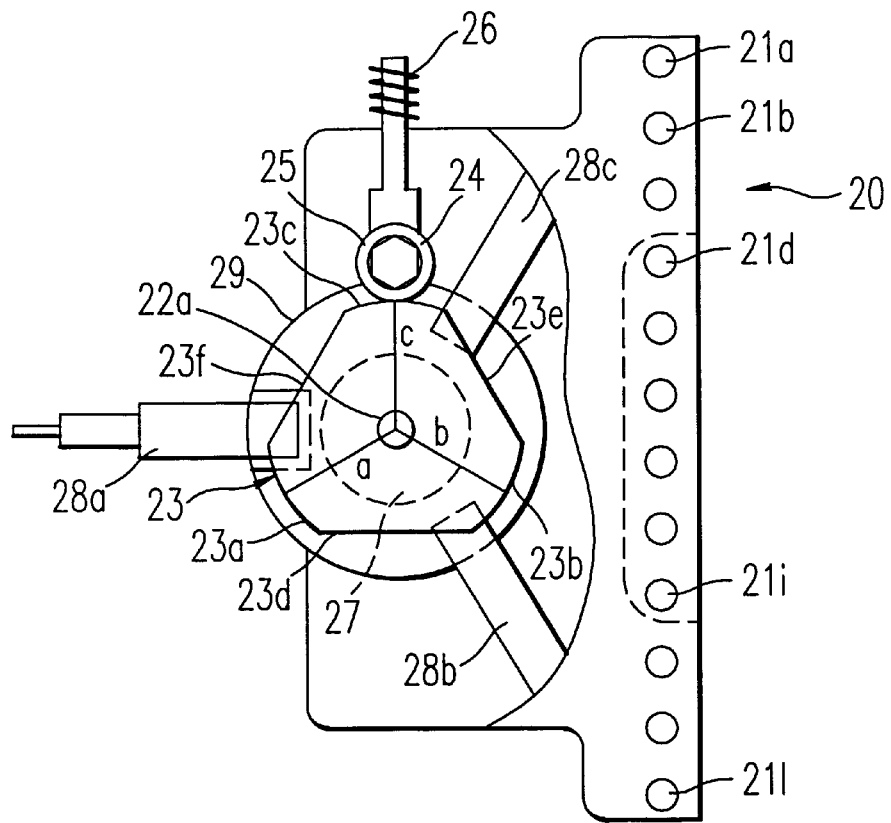
FIG. 3(b) is a plan view showing cam members and optical sensors of the essential part of the apparatus as shown in FIG. 3(a)
Figure 3C:
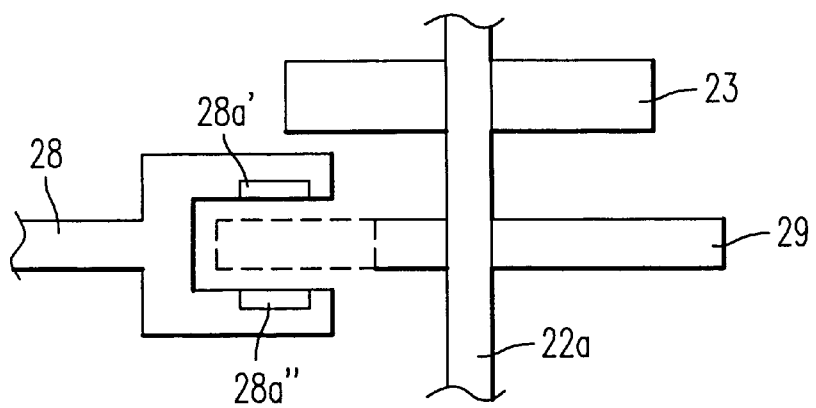
FIG. 3(c) is a sectional view of II–II' line of FIG. 3(a) showing cam members and optical sensors of the essential part of the apparatus.

For example, as shown in FIG. 3(c), when the cutout portion 30 is rotated to a position being in registry with the sensor 28a, a light emitted from a emitting portion 28a' is received by a receiving portion 28a" to activate the optical sensor so as to conduct the above control. In addition, as shown in FIG. 3(b) distances c, b and a between positions where the optical sensors 28a, 28b and 28c are contacted with the rotor 24 and the center of the rotating shaft 22a, respectively, are a little different so as to move the sensor block 20 three times within the scope of the well at a predetermined distance to measure the length of the precipitation pattern due to the flow of the particles at three sections of each of the well.

The above-described apparatus 10 for measuring precipitation patterns is used to implement the method of the present invention for indirect agglutination immunoassay, which is described below more specifically.

Figure 4A:
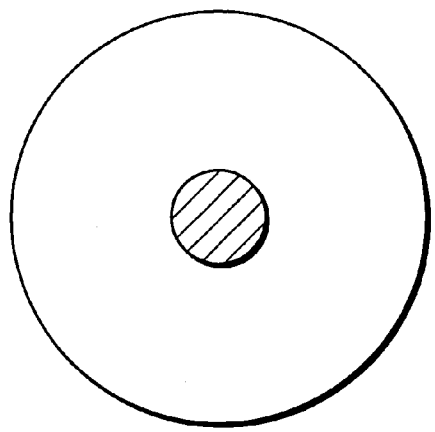
FIG. 4(a) is a plan view showing that a reagent in the well is precipitated by a magnet force before inclining the well.
Figure 4B:
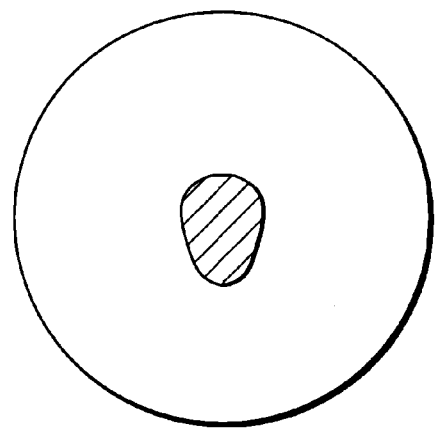
FIG. 4(b) is a plan view showing a precipitation pattern of a reagent after inclining the well when its reaction is positive.
Figure 4C:
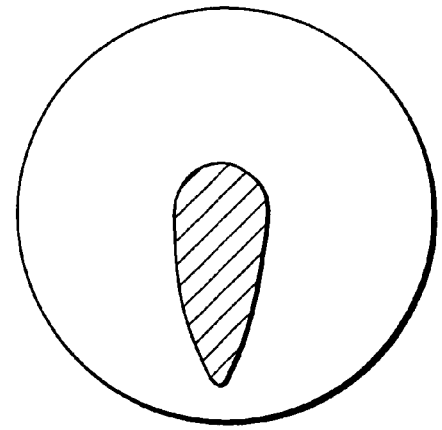
FIG. 4(c) is a plan view showing a precipitation pattern of a reagent after inclining the well when its reaction is negative.

In this embodiment, as shown in FIG. 4(a), a reagent including a component containing magnetic particles or particles containing a magnetic medium of the regent for immunoassay is precipitated by the magnet force. When the well including thus precipitated pattern therein is inclined at angle of 60°, the precipitation pattern does not flow if its reaction is positive as shown in FIG. 4(b) and it flows if its reaction is negative as shown in FIG. 4(c).

The apparatus 10 for measuring precipitation patterns has the micro plate 15 carried on the micro plate holder 14. The micro plate 15 has wells with U- or V-shaped bottoms in which a component containing magnetic particles or particles containing a magnetic medium as a reagent for immunoassay is allowed to precipitate in the central parts of the bottoms of the respective wells by magnetic force or the like. A problem with the micro plate 15 to be used in the present invention is that distortions occur in the edges around the bottoms of wells during plate molding since they have to be formed in a U- or V-shape and, hence, the wells do not necessarily lie in one line in either the longitudinal or transverse direction of the micro plate.

Figure 4D:
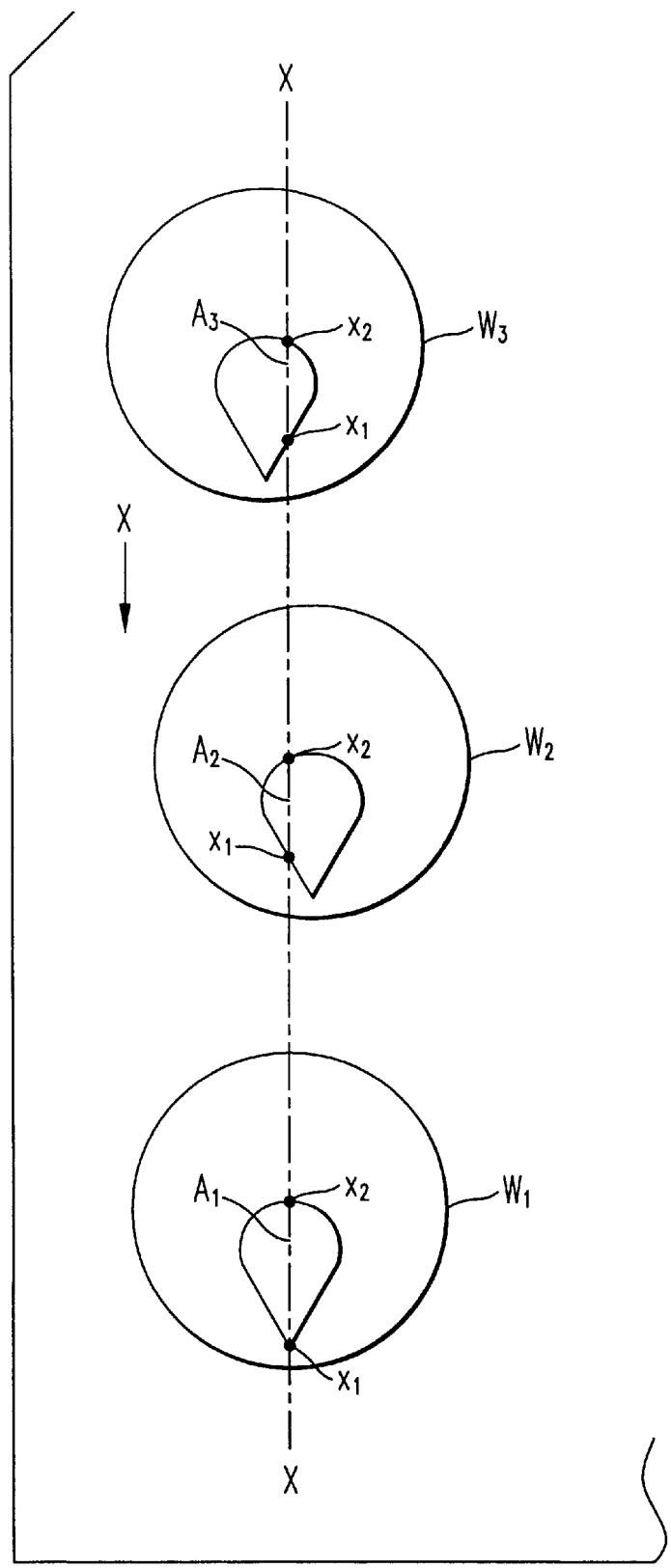
FIG. 4 (d) is a plan view showing how the lengths of precipitation patterns to be measured vary with the offset in the pitch between adjacent wells in a micro plate.
Figure 5:
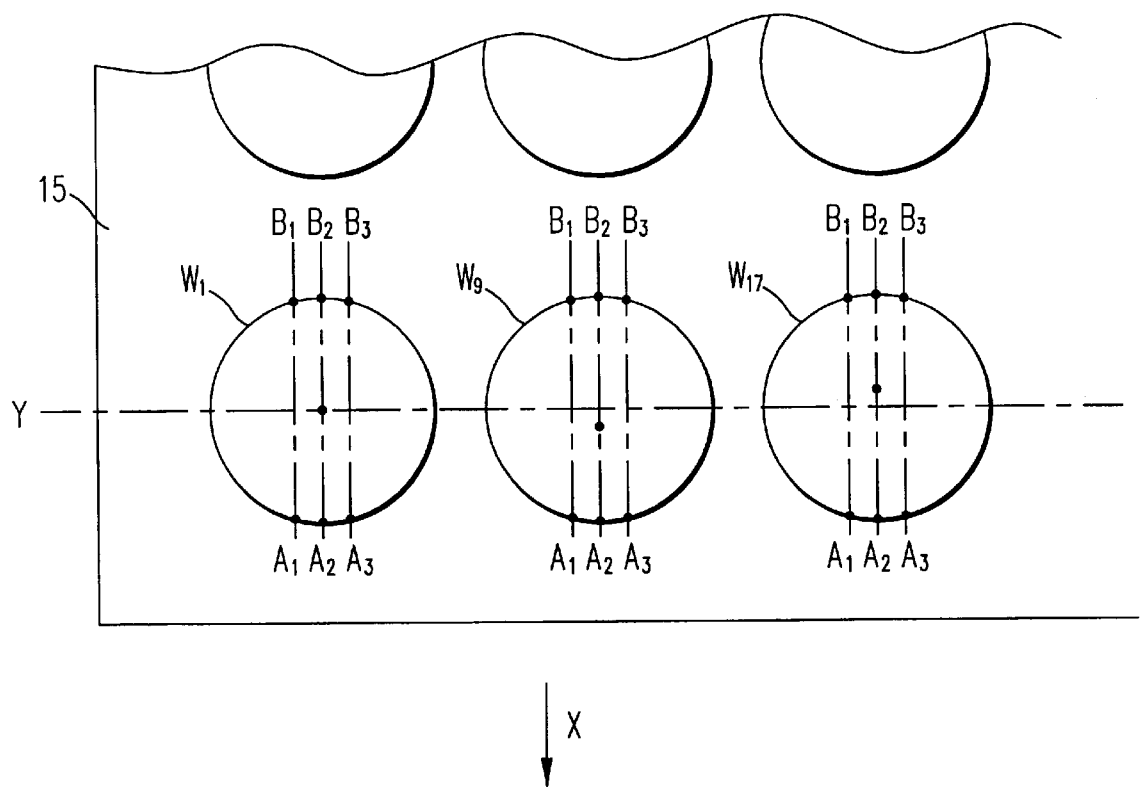
FIG. 5 is a plan view showing the sections to be searched for each well when measuring the lengths of precipitation patterns, as taken in the direction of the formation of precipitation patterns.

Therefore, if the lengths of precipitation patterns due to the flow of the particles are to be measured with the micro plate 15 being moved in the direction of X axis as shown in FIG. 4(d), optical sensors may be so set that they pass through the centers of the bottoms of the wells that are located in the most forward position in the direction of movement of the micro plate; in this case, the precipitation pattern due to the flow of the particles $A_1$ in the well $W_1$ at the most forward end can be measured correctly with optical sensors in two points $x_1$ and $x_2$ that lie on line X, or the path swept out by sensors.

However, if the wells are not in exact alignment and if the center of well $W_2$ is offset to the right of locus line X or if the center of well $W_3$ is offset to the left of locus line X, the length of precipitation pattern due to the flow of the particles $A_2$ or $A_3$ is measured incorrectly and their measured lengths come out shorter than the actual values.

Hence, in the method of the present invention for the indirect agglutination immunoassay, the precipitation patterns flowing to collect in the bottom of wells with using the optical fiber is measured following manner so as to collect any errors occurred on account of misalignment in the wells due to the molding distortions which is developed in edge portions around the bottoms of wells. Before the formation of precipitation patterns due to the flow of particles, the coordinates of predetermined sections to be searched for the measurement of the length of the precipitation pattern due to the flow of the particles in each well is stored in advance in a computer. Thereafter, after the formation of the precipitation patterns due to the flow of the particles, the length of the patterns are measured at a plurality of sections. Results of both measurements is compared each other, and the occurrence of an immunoreaction is judged based on the longest precipitation pattern due to the flow of the particles in the measurements.

Stated more specifically, the method of the present invention for indirect agglutination immunoassay is performed by the following procedure. First, as shown in FIG. 1, the micro plate 15 which is so processed that particles are allowed to precipitate in the bottoms of wells is carried on the micro plate holder 14 in such a way that the wells in columns cross vertically the direction in which the micro plate holder 14 slides on the base body 11. Then, before the base body 11 is inclined at a specified angle to form precipitation patterns due to the flow of the particles in the wells, the micro plate holder 14 is slid on the base body 11 in the X direction along the guide rods 13 until it is located above the sensor block 20 which is provided with the same number of optical sensors $21a, \ldots 21l$ as the wells in a column in the micro plate 15.

Then, the lengths of sections $A_1$ to $B_1$, $A_2$ to $B_2$ and $A_3$ to $B_3$ of the circles defining the peripheral edges of the bottoms of well $W_1$, well $W_9$, well $W_{17}, \ldots$ well $W_{8-7}$ ($1 \leq n \leq 12$) which are situated in the first column in the direction of movement of the micro plate 15 are measured for the total of ninety six wells that are present in the micro plate.

To this end, the sensor block 20 is moved by the drive of the cam member and any other necessary components in small distances (about 0.1 mm) in the Y direction, or the direction vertical to the direction of movement of the micro plate 15 and three measurements are performed on each well.

In addition, the measurement of the sections to be searched for the measurement of the length of precipitation patterns due to the flow of the particles can be omitted if the formation of the well in the micro plate is good sufficiently. However, in a similar measurement, an error of the result of the measurement of the length can be prevented. For example, if a fault such as bubble, a turbid solution, dust or the like exists in a well, the optical sensor detects the fault so as to measure the well detected the fault again. Namely, before the inclination of the well, the optical sensor measures a plurality of sections of the well within the scope of the well to detect the fault in the well. Further, whether the fault is in a well or not can be judged by a micro computer or the like provided on the apparatus. In this embodiment, at the same time of the measurement of sections to be searched for the measurement of the length of the precipitation pattern due to the flow of the particles, the detection of the fault in the well can be conducted. Needless to say, the measurements can be conducted separately.

When the measurement of the sections to be searched for the measurement of the lengths of precipitation patterns of the flow of the particles finishes for each well, the micro plate holder 14 is returned to the initial position and the base body 11 is inclined at an angle of about 60°, whereupon the precipitation patterns due to the flow of the particles is formed in the bottoms of the individual wells.

Figure 6:
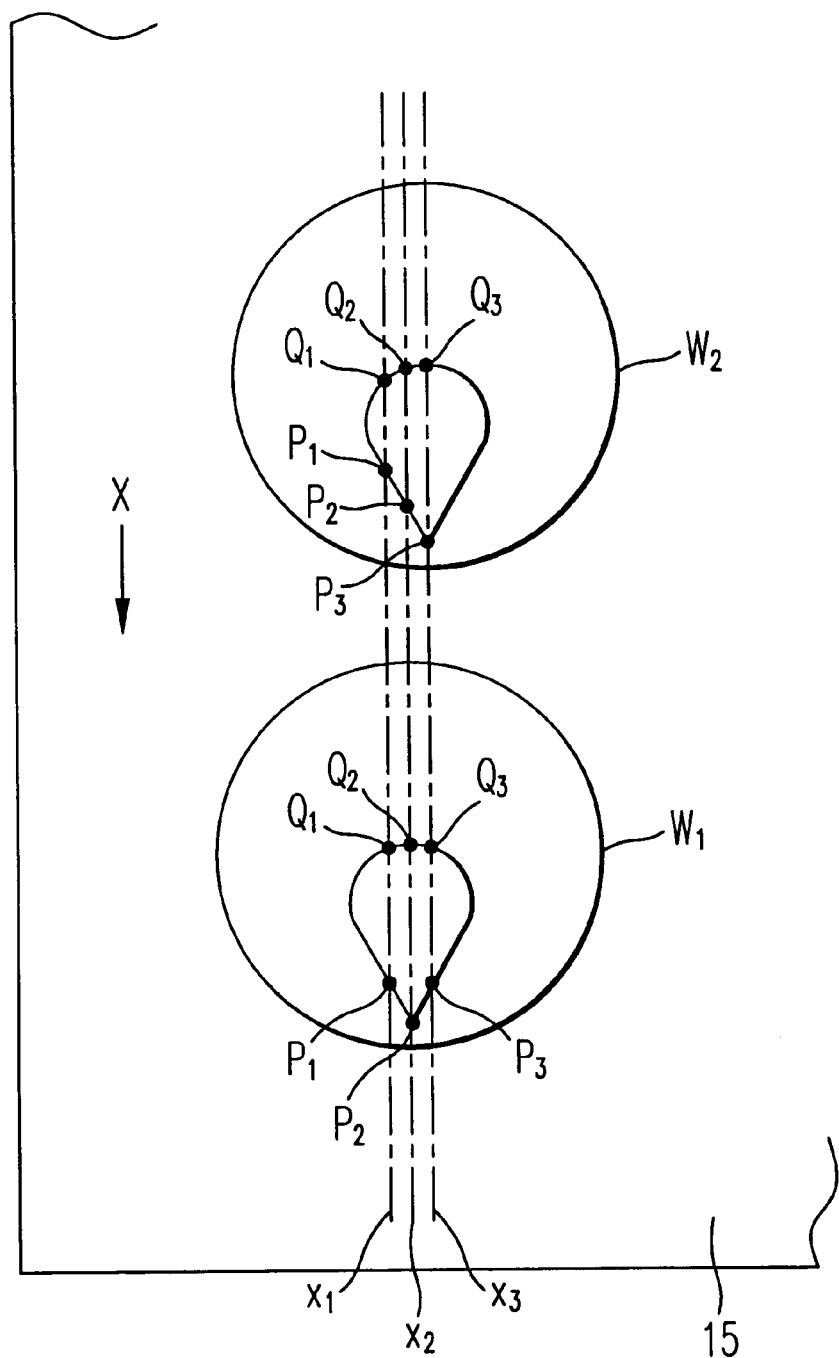
FIG. 6 is a plan view showing the process in which the lengths of formed precipitation patterns are measured.

When the formation of precipitation patterns due to the flow of the particles finishes, the base body 11 is restored to the initial horizontal state and, thereafter, the micro plate holder 14 is moved until the well W1 in the first column in the micro plate 15 is situated above the sensor block 20. Then, as shown in FIG. 6, the length of the precipitation pattern due to the flow of the particles in that well is measured over the distance from $P_1$ to $Q_1$ on line $X_1$, over the distance from $P_2$ to $Q_2$ on line $X_2$, and over the distance from $P_3$ to $Q_3$ on line $X_3$.

It is noted here that line $X_2$ refers basically to the center line of each well whereas lines $X_1$ and $X_3$ refer to off-center lines, and line $X_2$ presents between lines $X_1$ and $X_3$.

To measure the length of the precipitation pattern due to the flow of the particles at three locations in each well, the sensor block 20 is moved by small distances (at spacings of about 0.1 mm) in the Y direction and the measurements are performed for all of the wells into which the sample solution is injected; in the case under consideration, the measurements are conducted for all of the ninety six wells that are formed in the micro plate 15.

When implementing the method of the present invention, the sensors 18a, 18b, . . . 18h projecting from a lateral side of the micro plate holder 14 make successive contact with the measurement position sensors 19 which are provided downstream the direction of movement, whereupon the micro plate holder 14 advances in the X direction transversely by small increments corresponding to the pitch between two adjacent columns of wells. In addition, in this apparatus for indirect agglutination immunoassay, the micro plate holder 14 may not move but the sensor block 20 may move so as to conduct the measurement described above.

When the measurement of the lengths of precipitation pasterns in offset positions finishes for all of the ninety six wells formed in the micro plate 15, the measured values are compared on a computer with the values of the measurements that were conducted before the formation of the precipitation patterns due to the flow of the particles and the longest value of measured length values is used as a criterion in judging for the occurrence of an immunoreaction in each well.

Another embodiment of the method and apparatus for indirect agglutination immunoassay of the present invention in which a micro plate has a plurality of wells each having a flat shaped bottom will be described as follows specifically referring with the accompanying drawings.

The method of this embodiment is to be performed using a micro plate in which a number of wells each having a circular cross section and a specified depth with a flat bottom are formed in alignment in both longitudinal and transverse direction.

In this embodiment, the micro plate including a plurality of wells each having a flat shaped bottom is applied to the apparatus for indirect agglutination immunoassay 10' having a magnet unit 104 as shown in FIG. 1(b). However, the inclination mechanism does not always need to be provided with the apparatus. Further, the function, movement and the like of the elements of the apparatus is not limited by the former embodiment, but they perform suitable function, movement and the like in this embodiment as described below.

Figure 7:
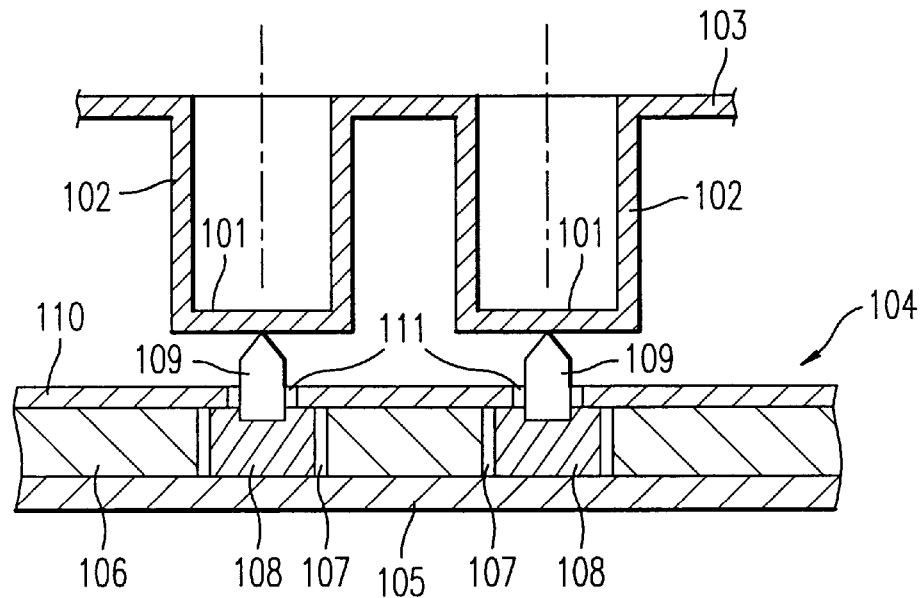
FIG. 7 is a sectional view showing the essential part of the apparatus which is to be used in implementing the method of the present invention for indirect agglutination immunoassay.

As an example of this embodiment, a micro plate 103 in FIG. 7 is made of a synthetic resin and it has a total of ninety six wells 102, 102, . . . formed as integral parts in an array having twelve columns in the longitudinal direction by eight rows in the transverse direction. The bottom 101 of each well 102 is so formed as to be horizontal with respect to its vertical inner peripheral surface, namely, parallel to the imaginary plane across the opening of the well.

Figure 9:
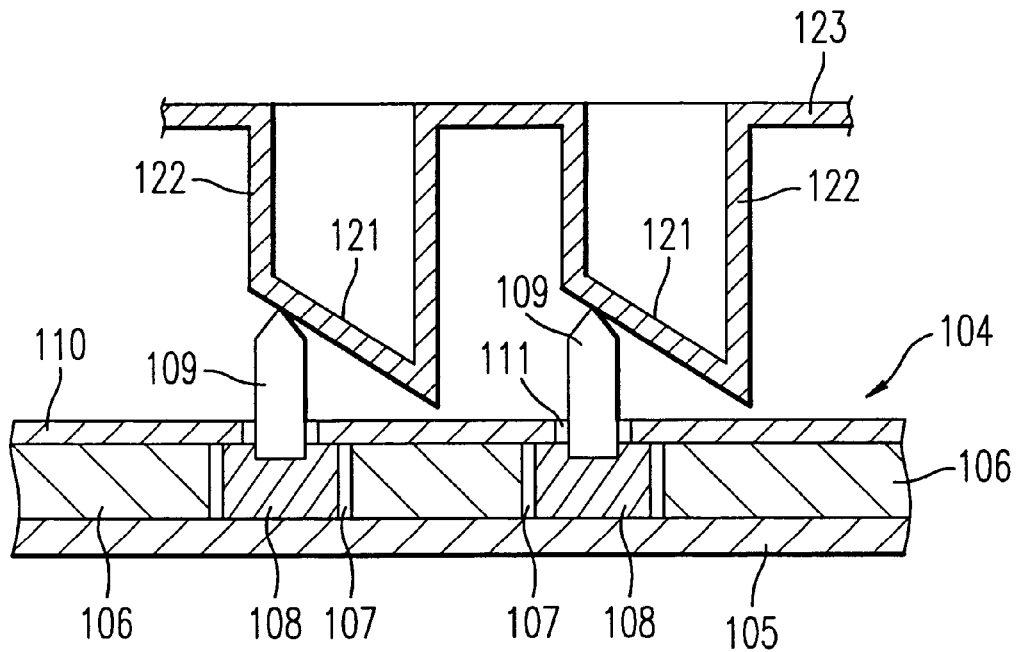
FIG. 9 is a sectional view showing the essential part of the apparatus which is to be used in implementing the method of the present invention for indirect agglutination immunoassay.
Figure 10:
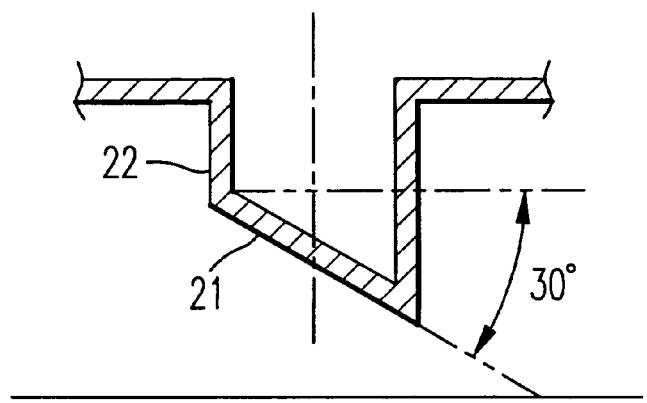
FIG. 10 is a sectional view showing schematically the micro plate used in the apparatus shown in FIG. 9.

In addition, a micro plate 123 in FIG. 9 is also made of a synthetic resin and it has a total of ninety six wells 122, 122, . . . formed as integral parts in an array including twelve columns in the longitudinal direction by eight rows in the transverse direction. The bottom 121 of each well 122 is so formed as to slope downward from its vertical inner peripheral surface on one side to the same vertical inner peripheral surface on the other side at an angle of about 30° with respect to the horizontal direction.

The micro plate 103 (or 123) is used in the following manner: a sample for immunoassay is injected into each well 102 (or 122) and, thereafter, a diluting solution is added to dilute the sample by a predetermined factor; then, a reagent containing magnetic particles or a magnetic medium is added to the diluted sample solution and the mixture is stirred to carry out an immunoreaction for a predetermined time; thereafter, a magnet is used to allow the component particles to precipitate at a specified site in the bottom 101 (or 121) of each well 102 (or 122).

As shown in FIG. 7 the magnet unit 104 which allows the component particles to precipitate in a specified position in the bottom of each well in the micro plate includes: a base body 105 made of an iron plate; a retainer plate 106 in the form of a polyvinyl chloride plate that is mounted on the base body 105; magnets 108 that are retained in holes 107 formed through the retainer plate 106 in positions that correspond to the wells in the micro plate; and a cover member 110 in the form of a polyvinyl chloride plate that covers the retainer plate 106 including the magnets 108, except in areas where adapters 109 project from the top of the magnets 108 through the cover member.

The retainer plate 106 has a plurality of holes 107, 107, . . . formed in positions corresponding to the respective wells 102 in the micro plate 103; the magnets 108 are to be retained in those holes by being fitted therein.

The magnets 108 are each in the form of a disk having a smaller diameter than the inside diameter of cylindrical well 102. The top of each magnet is detachably fitted in the center with the adapter 109 made of a magnetizable material and having a sharp-pointed tip.

The cover member 110 has holes 111, 111, . . . formed in positions that correspond to the respective wells 102 in the micro plate 103 and through which the adapters 109 on the magnets 108 project in positions corresponding to the centers of the bottoms 104 of the respective wells 102.

The magnet unit 104 is fabricated by the following procedure. First, the retainer plate 106 is placed on the base body 105; then magnets 108 are fitted into the holes 107 in the retainer plate 106 so that the magnets 108 are attracted and fixed to the base body 105, and the base body 105 made of an iron plate is magnetized to insure that the particles are allowed to precipitate more efficiently by the adapters 109. Next, the cover member 110 is mounted on the retainer plate 106 as the adapters 109 on the magnets 108 are passed through holes 111, whereby the magnet unit 104 is assembled with the cover member 110 covering all the surfaces of the magnets 108 except in areas where the adapters 109 project through it.

Thereafter, the micro plate 103 in which the sample and the reagent is mixed by an agitator is set up on the magnet unit 104 so that the tip end of each adapter 109 coincides with the center of the bottom 101 of each well. As a result, the magnetic particles in each well 102 are attracted to the center of its bottom 104 corresponding to the tip of adapter 109 by the magnetic action of magnet 108 working through the tip of its adapter 109.

The once precipitated particles of the respective components stays as fixed in the center of the bottom of each well even if the micro plate 103 is separated from the magnet unit 104 to be held in a magnetism-free state.

Then, the micro plate 103 is inclined at an angle of about 60° by pivoting along the edge of either one end of its longer sides, whereupon the component particles concentrating in the center of the bottom 1 of each well flow down the slope of the bottom toward the side wall on the other side, thereby forming a spindle-shaped precipitation pattern.

Figure 8:
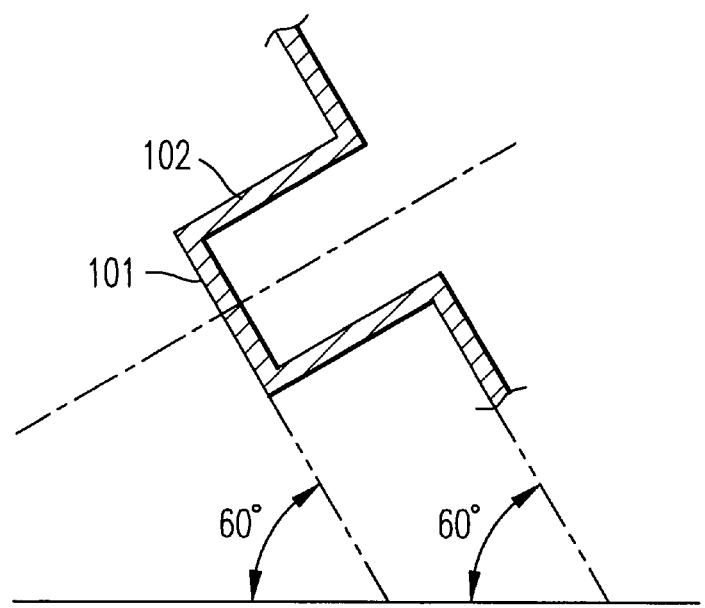
FIG. 8 is a sectional view showing schematically how the micro plate used in the apparatus shown in FIG. 7 looks like if it is inclined.

As shown in FIG. 8, the bottoms of the wells in the micro plate 103 are inclined at an angle of about 60° and, therefore, the particles in the wells flow down in wide streams at a comparatively slow speed. Accordingly, after the micro plate 103 is reverted to the initial horizontal position, the precipitation patters which is formed by the flow of the particles evaluate clearly to distinguish between the negative and positive states.

FIG. 9 shows an example in which the apparatus for indirect agglutination immunoassay is to be performed using the micro plate 123 in which the bottom 121 of each well 122 is so formed as to slope downward from the vertical inner peripheral surface on one side to the same vertical inner peripheral surface on the other side at an angle of about 30° with respect to the imaginary horizontal plane across the opening of the well.

This method of indirect agglutination immunoassay is implemented with the magnet unit 104 for indirect agglutination immunoassay which is basically of the same type as used in the described example above, except that adapters 109 are arranged in such a way that the tip of each adapter is positioned at the site where the bottom 121 of each well 122 in the micro plate 123 starts to slope downward, namely, below the bottom 121 in the highest position of the slope. If the micro plate 123 in which the sample is mixed with the reagent component in each well 122 is set up on the magnet unit 104, the magnetic particles in each well 122 are allowed to precipitate as they are attracted to the higher position of the slope of the bottom 121 corresponding to the tip of each adapter 109 by the magnetic action of each magnet 108 working through the tip of the adapter 109.

After the particles is thus allowed to precipitate in that area of the bottom of well 122 which is in the higher position of the slope, the micro plate 122 is separated from the magnet 108 so that the precipitated particles is free from the influence of the magnet; as a result, the particles flow downward in a stream of a certain width along the inclined flat surface of the bottom 121 of well 122.

In this example under consideration, the bottom 121 of each well 122 is inclined at an angle of about 30°; therefore, if the micro plate 123 is inclined backward by an angle of about 30° until the bottom 121 becomes horizontal and if it is held in that horizontal state, the measurement of precipitation patterns due to the flow of the particles can be accomplished more correctly without any defocusing problem.

Alternatively, precipitation patterns due to the flow of the particles can be measured on the horizontal micro plate 123, with optical sensors and the like being positioned parallel to the inclined bottom 121 of each well 122.

The method for indirect agglutination immunoassay of the present invention has an effect that even if the micro plate to be used involves errors in the pitch between adjacent wells that occurred due to the molding distortions in the edge portions around the bottoms of wells, the lengths of precipitation patterns due to the flow of the particles can be measured with high precision while, at the same time, the reproducibility of measurement data can be improved.

The apparatus for measuring precipitation patterns that is to be used with this method for indirect agglutination immunoassay has an effect that even if the pitch of wells involves errors that occurred during the molding of the micro plate, the sections to be searched for the measurement of the lengths of precipitation patterns and the lengths of precipitation patterns due to the flow of the particles can be measured correctly at a plurality of sections for each well by moving optical sensors within the scope of the well at a predetermined distance a plurality of times to measure the lengths of the precipitation pattern due to the flow of the particles in a direction vertical to the direction of movement of the micro plate.

The method of the present invention for indirect agglutination immunoassay uses flat-bottomed wells. Accordingly, the distance to optical sensors is invariable between the bottom of each well and its periphery and, hence, there is no possibility of defocusing even if optical sensors are used and the desired assay of immunoreaction can be performed with a simple and compact apparatus.

In addition, the precipitation patterns due to the flow of the particles are formed on the flat surfaces of the bottoms of wells and, hence, they can be made to assume a spindle shape having no sharp advancing end; therefore, the reproducibility of length measurements can be improved markedly.

Further, the particles can be allowed to precipitate in a specified position in each well with such accuracy that misalignment, if any, in the wells will cause no substantial problem for the purpose of measurements in practical situations and, at the same time, precipitation patterns that form in the bottoms of wells can be measured in a more simplified manner.

The apparatus of the present invention for indirect agglutination immunoassay is so constructed that magnets having adapters with sharp-pointed tips are arranged beneath the flat-bottomed wells in a micro plate and that the magnetic force of said magnets can be caused to act in specified positions under the bottoms of wells through the adapters. Because of this arrangement, the component particles can be allowed to precipitate as they are concentrated with accuracy in the specified positions in the bottoms of wells; at the same time, the precipitation patterns that are subsequently formed due to the flow of the particles can be made in the form of a spindle that has no sharp-pointed advancing end and which, hence, assures high reproducibility of data in measurements. Thus, the apparatus enables the results of immunoreactions to be evaluated in an advantageous manner.

In addition, the micro plate to be used in the apparatus of the present invention which has flat-bottomed wells has the advantage that the precision in the molding of wells need not be high and this contributes many practical advantages such as the ability to accomplish reasonably precise evaluation if only the sharp-pointed tips of adapters on the magnets in the apparatus for allowing particles to precipitate are oriented to coincide exactly with the centers of the bottoms of the associated wells.

The foregoing description of preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments and with various modifications as are suited to the particular use contemplated. It is intended that the scope of the invention be defined by the claims.

What is claimed is:

1. In an indirect agglutination assay method in which agglutination is caused by an antigen-antibody reaction employing magnetic particles, said particles having an antigen or antibody bound thereto which bind to an analyte which may be in a sample, the particles being attracted to a point in a container containing both the sample and particles under the influence of an applied magnetic force, which is removed to allow the particles to flow under the influence of gravity to form a precipitation pattern, wherein the length of the pattern is measured and then evaluated to judge the occurrence of an immunoreaction based on the length of the precipitation pattern, the improvement which comprises measuring the lengths of said precipitation pattern at a plurality of points within said container, comparing said measured lengths whit each other, selecting the longest length of the measured lengths as the length for said precipitation pattern, and determining whether the immunoreaction is positive or negative by comparing said length with a known standard.

2. The assay of claim 1, wherein said container has a closed bottom which is horizontal with respect to a vertical peripheral surface thereof and said applied magnetic force is applied to a center of said bottom.

3. The assay of claim 1, wherein said container has a closed bottom which is inclined in a single direction with respect to a vertical peripheral surface thereof and said magnetic force is applied to a point along said inclined bottom.

* * * * *